United States Patent
Giladi et al.

(10) Patent No.: US 10,821,283 B2
(45) Date of Patent: Nov. 3, 2020

(54) REDUCING MOTILITY OF CANCER CELLS USING TUMOR TREATING FIELDS (TTFIELDS)

(71) Applicant: Novocure Limited, St. Helier (JE)

(72) Inventors: Moshe Giladi, Moshav Herut (IL); Rosa S. Shnaiderman, Haifa (IL)

(73) Assignee: Novocure GmbH, Root (CH)

(*) Notice: Subject to any disclaimer, the term of this patent is extended or adjusted under 35 U.S.C. 154(b) by 694 days.

(21) Appl. No.: 15/478,066

(22) Filed: Apr. 3, 2017

(65) Prior Publication Data

US 2017/0281934 A1 Oct. 5, 2017

Related U.S. Application Data

(60) Provisional application No. 62/317,985, filed on Apr. 4, 2016.

(51) Int. Cl.
*A61B 18/12* (2006.01)
*A61N 1/32* (2006.01)
*A61N 1/40* (2006.01)
*A61N 1/00* (2006.01)

(52) U.S. Cl.
CPC ........ *A61N 1/32* (2013.01); *A61N 1/40* (2013.01)

(58) Field of Classification Search
CPC .................................. A61B 18/12; A61N 1/18
USPC ................. 607/2–3, 66, 75; 606/34
See application file for complete search history.

(56) References Cited

U.S. PATENT DOCUMENTS

| | | | |
|---|---|---|---|
| 6,278,895 B1 | 8/2001 | Bernard | |
| 6,868,289 B2 | 3/2005 | Palti | |
| 7,089,054 B2 | 8/2006 | Palti | |
| 7,706,890 B2 | 4/2010 | Palti | |
| 7,917,227 B2* | 3/2011 | Palti | A61N 1/40 607/66 |
| 8,019,414 B2* | 9/2011 | Palti | A61N 1/326 607/3 |
| 8,244,345 B2 | 8/2012 | Palti | |
| 2003/0191506 A1 | 10/2003 | Shloznikov | |
| 2014/0330268 A1 | 11/2014 | Palti et al. | |

FOREIGN PATENT DOCUMENTS

| | | |
|---|---|---|
| EP | 1502623 A1 | 2/2005 |
| EP | 1933937 A2 | 6/2008 |
| WO | 2006083625 A1 | 8/2006 |

OTHER PUBLICATIONS

International Search Report and Written Opinion for International Application No. PCT/IB2017/051898 dated Jun. 12, 2017.

* cited by examiner

*Primary Examiner* — Jon Eric C Morales
(74) *Attorney, Agent, or Firm* — Potomac Law Group, PLLC

(57) ABSTRACT

The spreading of cancer cells in a target region can be inhibited by imposing a first AC electric field in the target region for a first interval of time, with a frequency and amplitude selected to disrupt mitosis of the cancer cells; and imposing a second AC electric field in the target region for a second interval of time, with a frequency and the amplitude selected to reduce motility of the cancer cells. The amplitude of the second AC electric field is lower than the amplitude of the first AC electric field.

23 Claims, 5 Drawing Sheets

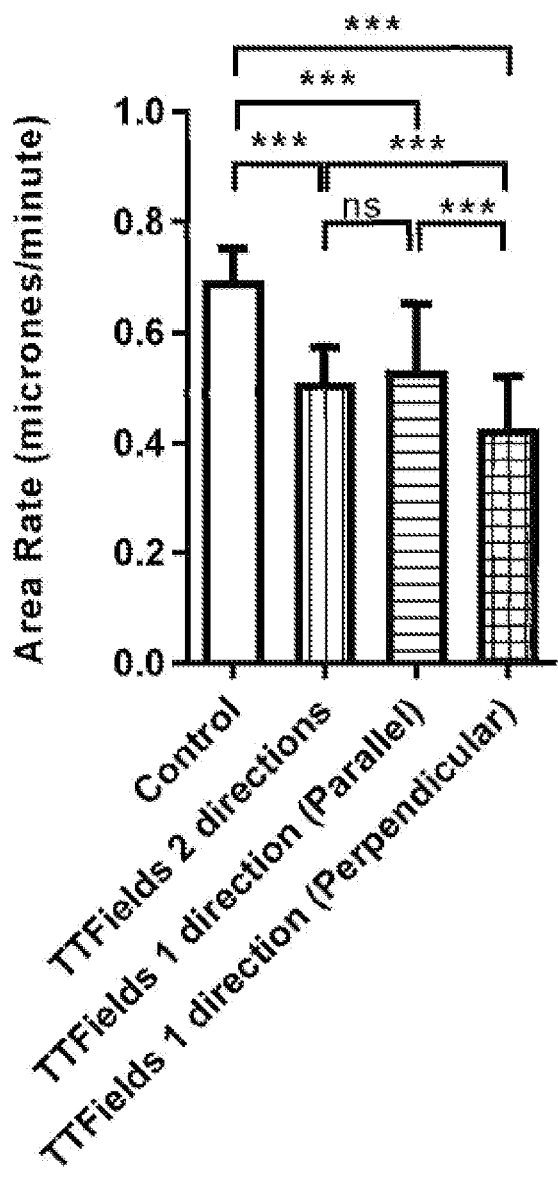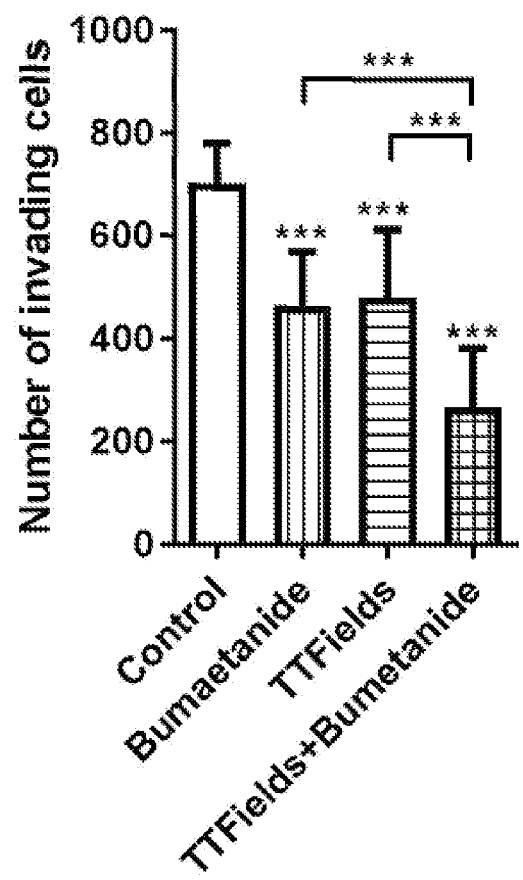
FIG. 5                                    FIG. 6

REDUCING MOTILITY OF CANCER CELLS USING TUMOR TREATING FIELDS (TTFIELDS)

CROSS REFERENCE TO RELATED APPLICATIONS

This Application claims the benefit of U.S. Provisional Application 62/317,985, filed Apr. 4, 2016, which is incorporated herein by reference in its entirety.

BACKGROUND

TTFields are an effective and FDA approved approach for treating tumors. Treatment using TTFields involves the continuous, noninvasive application of low intensity, intermediate frequency, alternating electric fields to a target region that includes the tumor. Previous investigations have shown that TTFields disrupt of microtubules and septin filaments, both of which govern key roles in mitosis.

Novocure's Optune® system is the current state of the art for treating glioblastoma using TTFields. Optune® uses a set of electrodes (also referred to as transducer arrays) that are positioned on a patient's body in the vicinity of the tumor. The Optune® field generator unit applies AC signals to those electrodes so as to induce an AC electric field in a target region that includes the tumor.

The Optune® system works best when the strength of the AC electric field in the tumor is >1 V/cm RMS, and increasing the field strength to between 2 and 3 V/cm RMS generally provides improved results. But thermal considerations often limit the strength of the AC electric field that can be delivered to the target region. More specifically, because the patient's skin must be protected from overheating, the Optune® system detects the temperature beneath the transducer arrays, and sometimes reduces the strength of the electric field to keep that temperature from exceeding 41° C. Unfortunately, the safety and comfort benefits provided by this temperature control tactic are accompanied by a drawback: the reduced-strength field is less effective at disrupting mitosis than a full-strength field.

SUMMARY OF THE INVENTION

One aspect of the invention is directed to a first method of inhibiting spreading of cancer cells in a target region. This method comprises (a) imposing a first AC electric field in the target region for a first interval of time, the first AC electric field having a first frequency and a first amplitude. The first frequency and the first amplitude are selected so that the first AC electric field disrupts mitosis of the cancer cells. This method also comprises (b) imposing a second AC electric field in the target region for a second interval of time, the second AC electric field having a second frequency and a second amplitude. The second frequency and the second amplitude are selected so that the second AC electric field reduces motility of the cancer cells, and the second amplitude is lower than the first amplitude. This method also comprises continuously repeating step (a) and step (b) in an alternating sequence during a course of treatment.

In some embodiments of the first method, the second amplitude is less than 75% of the first amplitude. Optionally, in these embodiments, the first interval of time is less than 5 seconds, and the second interval of time is less than 5 seconds. The course of treatment may a duration of at least 12 hours.

In some embodiments of the first method, the second frequency and the first frequency are different. In some embodiments of the first method, the first frequency is 200 kHz±10% and the second frequency is 300 kHz±10%.

In some embodiments, the first method further comprises the step of administering a compound that inhibits cell motility during the course of treatment. In some of these embodiments, the compound comprises Bumetanide.

In some embodiments of the first method, the second amplitude is at least 0.6 V/cm RMS.

In some embodiments of the first method, the second amplitude is less than 75% of the first amplitude, the second frequency and the first frequency are different, the first interval of time is less than 5 seconds, the second interval of time is less than 5 seconds, and the second amplitude is at least 0.6 V/cm RMS. Optionally in these embodiments, the first frequency is 200 kHz±10% and the second frequency is 300 kHz±10%.

In some embodiments of the first method, the first AC electric field is imposed in the target region in a first direction for a first portion of the first interval of time, the first AC electric field is imposed in the target region in a second direction for a second portion of the first interval of time, and an angle between the first direction and the second direction is between 60° and 90°. In some of these embodiments, the second AC electric field is imposed in the target region in the first direction for a first portion of the second interval of time, and the second AC electric field is imposed in the target region in the second direction for a second portion of the second interval of time. In some of these embodiments, the second amplitude is less than 75% of the first amplitude. In some of these embodiments, the second frequency and the first frequency are different, the first interval of time is less than 5 seconds, and the second interval of time is less than 5 seconds.

In some embodiments of the first method, a direction of the first AC electric field is changed during at least some of the repeating steps, and a direction of the second AC electric field is changed during at least some of the repeating steps. In some of these embodiments, the second amplitude is less than 75% of the first amplitude. In some of these embodiments, the second frequency and the first frequency are different, the first interval of time is less than 5 seconds, and the second interval of time is less than 5 seconds.

Another aspect of the invention is directed to a second method of inhibiting spreading of cancer cells in a target region. This method comprises (a) imposing a first AC electric field in the target region, the first AC electric field having a first frequency and a first amplitude. The first frequency and the first amplitude are selected so that the first AC electric field disrupts mitosis of the cancer cells. This method also comprises (b) imposing a second AC electric field in the target region, the second AC electric field having a second frequency and a second amplitude. The second frequency and the second amplitude are selected so that the second AC electric field reduces motility of the cancer cells. The second frequency and the first frequency are different, and the second amplitude is lower than the first amplitude.

In some embodiments of the second method, the second amplitude is less than 75% of the first amplitude.

Another aspect of the invention is directed to a first apparatus for inhibiting spreading of cancer cells in a target region. This apparatus comprises an AC signal generator having (i) a first controllable output configured to apply an AC voltage across a first set of capacitively coupled electrodes that are positioned in a vicinity of the target region, so as to impose an electric field in the target region in a first direction and (ii) a second controllable output configured to apply an AC voltage across a second set of capacitively coupled electrodes that are positioned in the vicinity of the target region, so as to impose an electric field in the target region in a second direction. This apparatus also comprises a controller configured to (a) control the first controllable output so that a first AC signal is generated for a first interval of time, the first AC signal having a first frequency and a first amplitude. The first frequency and the first amplitude are selected to impose an electric field that disrupts mitosis of the cancer cells. The controller is also configured to (b) control the first controllable output so that a second AC signal is generated for a second interval of time, the second AC signal having a second frequency and a second amplitude. The second frequency and the second amplitude are selected to impose an electric field that reduces motility of the cancer cells, and the second amplitude is lower than the first amplitude. The controller is also configured to (c) control the second controllable output so that a third AC signal is generated for a third interval of time, the third AC signal having a third frequency and a third amplitude. The third frequency and the third amplitude are selected to impose an electric field that disrupts mitosis of the cancer cells. The controller is also configured to (d) control the second controllable output so that a fourth AC signal is generated for a fourth interval of time. The fourth AC signal has a fourth frequency and a fourth amplitude. The fourth frequency and the fourth amplitude are selected to impose an electric field that reduces motility of the cancer cells, and the fourth amplitude is lower than the third amplitude. The controller is also configured to continuously repeat (a) through (d) in an alternating sequence during a course of treatment.

In some embodiments of the first apparatus, the second amplitude is less than 75% of the first amplitude and the fourth amplitude is less than 75% of the third amplitude. In some embodiments of the first apparatus, the second frequency and the first frequency are different, and the fourth frequency and the third frequency are different.

In some embodiments of the first apparatus, the second amplitude is less than 75% of the first amplitude, the fourth amplitude is less than 75% of the third amplitude, the second frequency and the first frequency are different, the fourth frequency and the third frequency are different, the third frequency is the same as the first frequency, the fourth frequency is the same as the second frequency, the first interval of time is less than 5 seconds, the second interval of time is less than 5 seconds, the third interval of time is less than 5 seconds, and the fourth interval of time is less than 5 seconds.

In some embodiments of the first apparatus, the first frequency is 200 kHz±10%, the second frequency is 300 kHz±10%, the third frequency is 200 kHz±10%, and the fourth frequency is 300 kHz±10%.

BRIEF DESCRIPTION OF THE DRAWINGS

FIG. 5 depicts the results of cell migration rate experiments that studied the directional dependence of TTFields' inhibition of glioma cancer cells.

FIG. 6 depicts the results of cell invasion experiments that compares the efficacy of TTFields to the efficacy of Bumetanide in inhibiting glioma cancer cells.

DESCRIPTION OF THE PREFERRED EMBODIMENTS

The ability of glioblastoma cells to invade adjacent brain tissue can make it difficult to control glioblastoma. The development of treatment modalities that hinder glioma cancer cell motility could therefore facilitate disease control.

The inventors have determined that, in addition to having antimitotic effects, TTFields have an impact on other cellular processes that require proper microtubule dynamics. One such process, which has a major impact on glioblastoma progression, is cell motility. This application documents the effects of TTFields on cell motility, including both the migration and invasion properties of glioma cells. This application also describes methods and systems for reducing cell motility by applying TTFields to cancer cells in a target region.

A set of experiments was run to evaluate the effect of TTFields on human glioma cell motility, including the migration and invasion properties of those cells.

Figure 1:
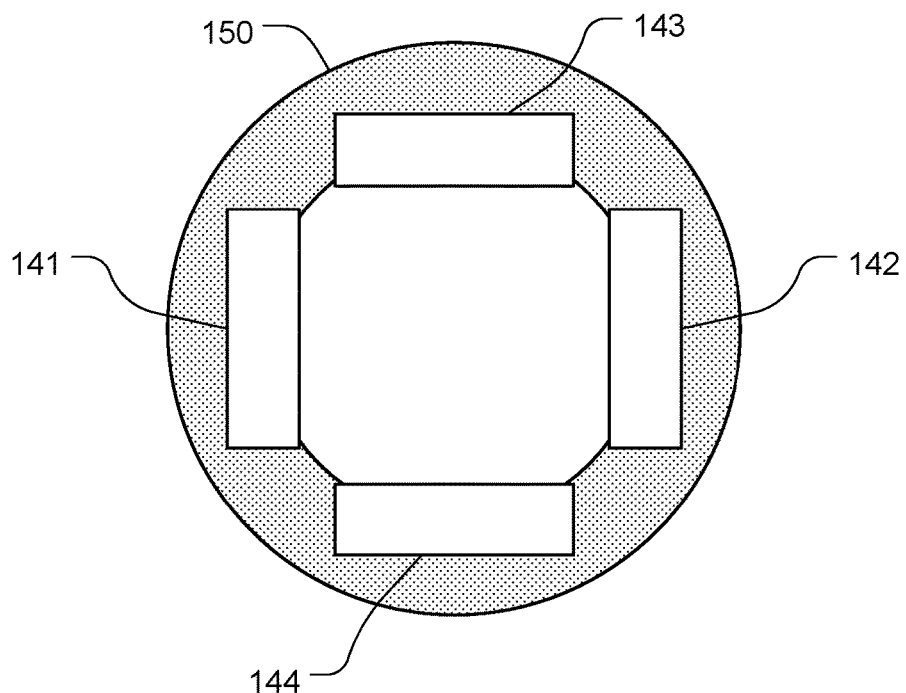
FIG. 1 depicts an arrangement of electrodes in a Petri dish used to conduct some of the experiments described herein.

The first experiment used scratch wound assays in vitro to determine the effects of TTFields on migration of U-87 MG and A-172 glioma cells. In this experiment, in vitro wound assays were performed using IBIDI culture-inserts. TTFields (200 kHz, 1.75 RMS) were applied using two pairs of electrodes 141-142 and 143-144 that were insulated by a high dielectric constant ceramic ($\epsilon$>5000) (Exelis, Salt Lake City, Utah). The electrode pairs 141-142 and 143-144 were positioned in the Petri dish 150 perpendicular to each other with the geometry depicted in FIG. 1. The electrodes 141-143 were connected to a modified Novocure Optune® system, which applied the appropriate AC signals to the electrodes 141-143 in order to generate TTFields in the target region. The TTFields changed direction by 90° every 1 second. This was accomplished by (a) applying the AC signal between electrodes 141 and 142 for 1 s, then (b) applying the AC signal between electrodes 143 and 144 for 1 s, and then repeating that (a)+(b) sequence for the course of the experiment. Temperature was measured by thermistors (not shown) incorporated into the dishes 150.

The U-87 MG and A-172 cells were scratched and imaged. Migration was observed in time-lapse series for 24 h (Zeiss axio observer; per 10 objective). Phase contrast images were recorded every 12 min. Baseline images of the scratch at 0 hours and cells that migrated into the scratch area 14 hours later were examined, at the same reference points. The obtained images were further evaluated to quantify cell migration rates during wound healing using the Image Pro Premier (Media Cybernetics, USA) software. Quantitative analysis of migration rate was performed, calculated as the total distance that the cells moved from the edge of the scratch toward the mid-center of the scratch as a function of time.

Figure 2A:
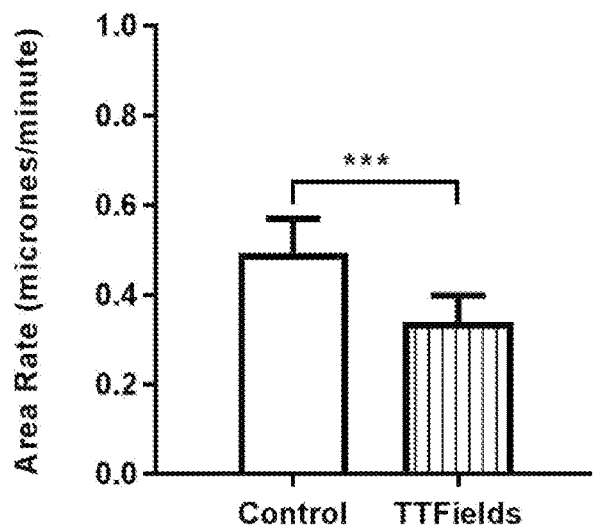
FIGS. 2A and 2B depicts the results of cell migration rate experiments that studied TTFields' effects on two different cell lines.
Figure 2B:
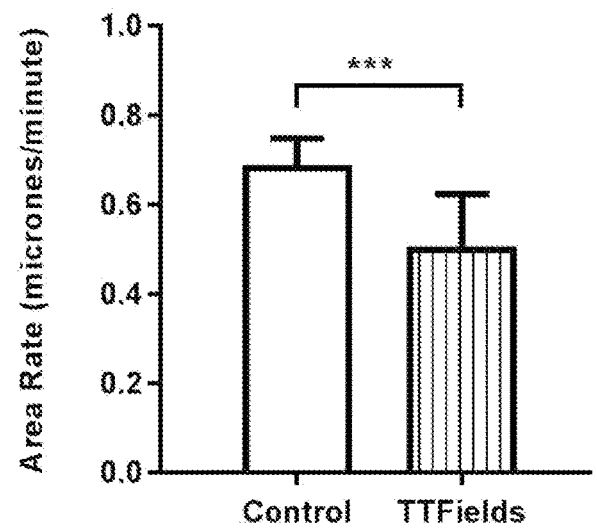

FIGS. 2A and 2B summarize the results of the quantitative analysis for this first experiment. Cell migration rate was significantly reduced in TTFields treated U-87 MG (31%) and A-172 (27%) cell lines, compared with untreated control cells, as seen in FIG. 2A and FIG. 2B, respectively (mean+ SEM; ***p <0.001 from control group, student's t-test). The experiment was repeated 3 times. These results indicate that TTFields hinder cell migration in different glioma cell lines.

In a second experiment, an invasion assay was performed using a modified Boyden chamber to determine the effects of TTFields on invasion for U-87 MG, A-172, LN-229 and LN-18 cells. Filters (6.4 mm in diameter, 8 µm pore size) coated with Matrigel (Corning) were used. TTFields were applied using the Novocure Inovitro system by means of perpendicular pairs of electrodes insulated by a high dielectric constant ceramic (200 kHz, 0.6 V/cm RMS). The geometry of the electrodes for this experiment was similar to the geometry depicted in FIG. 1, and the direction of the field was switched every 1 s (as described above for the first experiment). Inovitro dishes with extended vertical walls were used to facilitate effective delivery of TTFields through the transwell. The U-87 MG, A-172, LN-229 and LN-18 cells ($2 \times 10^5$) were suspended in serum free DMEM and seeded on the upper compartment of the chamber. The lower compartment contained 10% FBS DMEM. After incubation for 24 hours at 37° C. in a 5% CO2 incubator, the cells that invaded to the bottom filter, were fixed with 4% PFA, stained with 0.5% crystal violet (Sigma) and imaged under inverted microscope (Nikon eclipse TS100; upper panel-control, Lower panel-TTFields treated cells; Objective ×10). Quantification of invading cells was performed using ImageJ software (NIH).

Figure 3:
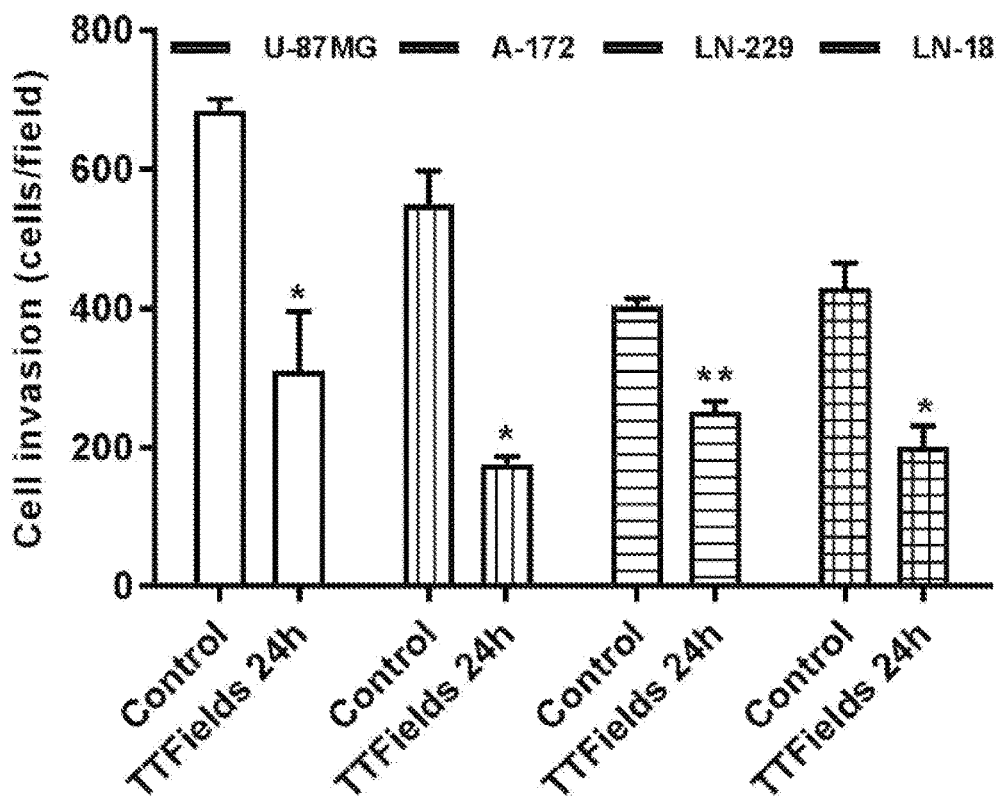
FIG. 3 depicts the results of cell invasion experiments that studied TTFields' effects on four different cell lines.

FIG. 3 summarizes the results of the quantification for this second experiment. The number of invading cells was significantly reduced in all TTFields treated cell lines: U-87 MG (54%), A-172 (68%), LN-229 (38%) and in LN-18 (55%) compared with untreated control cells (mean+SEM; *p<0.05, p<0.01, *p<0.001 from control group, student's t-test). These results indicate that TTFields hinder cell invasion in different glioma cell lines. It is noteworthy that duration of this invasion experiments (24 hours) was shorter than the duration (72 hours) that is ordinarily required for the anti-mitotic effect of TTFields. It was also noteworthy that the electric field intensity (i.e., 0.6 V/cm RMS) that caused this reduction in invasion was lower than the electric field intensity (i.e., >1 V/cm RMS) that is ordinarily required for the anti-mitotic effect of TTFields.

A third experiment was conducted to study the frequency dependence of TTFields' inhibition of U-87 glioma cancer cells invasive potential. A U-87 invasion assay was performed using modified Boyden chamber as described above in connection with the second experiment. TTFields were applied in various frequencies (100, 200, 300, and 400 kHz) using the same nominal intensity of 0.6 V/cm RMS and the same direction switching described above in connection with the first experiment. After incubation for 24 hours at 37° C. in a 5% CO2 incubator, the cells that invaded to the bottom filter were fixed, imaged and quantified as described above in connection with the second experiment.

Figure 4:
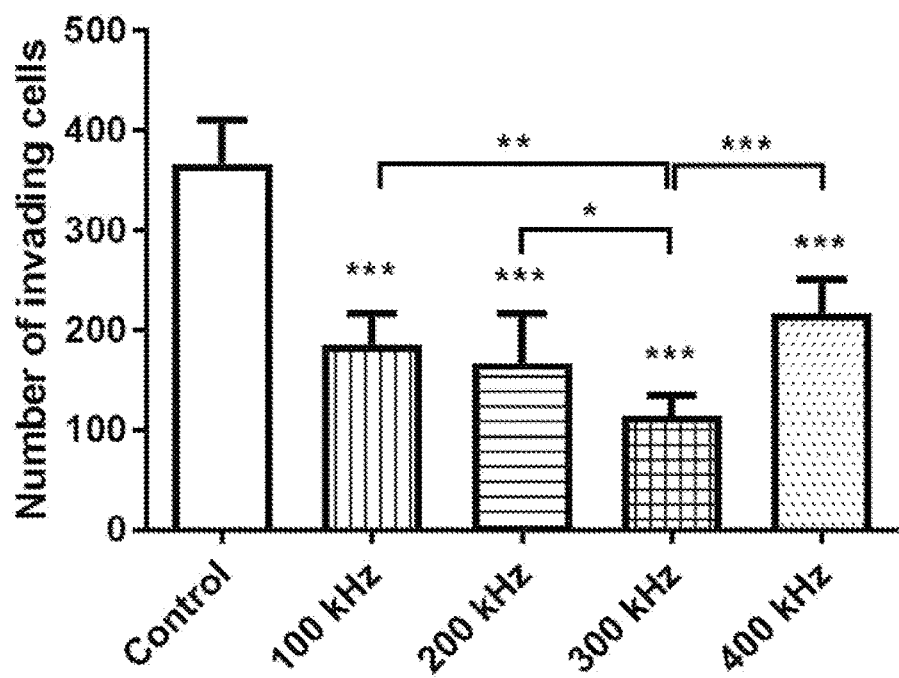
FIG. 4 depicts the results of cell invasion experiments that studied the frequency dependence of TTFields' inhibition of U-87 glioma.

FIG. 4 summarizes the results of the quantification for this third experiment. The number of invading cells was reduced (with respect to the control) for all four frequencies of TTFields tested in a frequency dependent manner; and the maximal reduction in the number of invading cells was observed at a frequency of 300 kHz. Perhaps most notably, the frequency that provided the highest reduction in the invasion potential was different from the 200 kHz frequency that provides (based on previous experiments) the highest anti-mitotic effect in U-87 cells.

A fourth experiment was conducted to study the directional dependence of TTFields' inhibition of glioma cancer cells migration. TTFields (200 kHz, 1.75 RMS) were applied using two pairs of electrodes, insulated by a high dielectric constant ceramic ($\varepsilon$>5000) (Exelis, Salt Lake City, Utah) positioned in the Petri dish. The geometry of the electron pairs was similar to the geometry shown in FIG. 1. In vitro wound assays were performed using IBIDI culture-inserts with 2 inserts placed in each dish, one in parallel with the electric field and one perpendicular to the direction of the electric field. The electrodes were connected to a modified Optune® system that applied AC signals to the electrodes in order to generate the electric field in the various directions required for this experiment. Temperature was measured by thermistors incorporated into the dishes.

A-172 cells were scratched in 2 perpendicular directions and imaged. Migration was observed in time-lapse series for 24 h as described. The obtained images were further evaluated to quantify cell migration rates during wound healing using the Image Pro Premier (Media Cybernetics, USA) software. Quantitative analysis of migration rate calculated as the total distance that the cells moved from the edge of the scratch toward the mid-center of the scratch as a function of time.

FIG. 5 summarizes the results of the quantitative analysis for this fourth experiment. Cell migration rate was significantly reduced in as compared to the control when cells were migrating in parallel (24%) with the electric field, which was similar to the reduction obtained when the TTFields were applied from two different directions and switched every second (27%). Interestingly, TTFields applied from a single direction, perpendicular to the migration course, resulted in the highest reduction in the migration rate (39%) which was significantly higher than the reduction obtained when TTFields were applied in two directions or a single direction in parallel with the course of migration (***p<0.001 from both groups, student's t-test. The experiment was repeated 3 times). These results indicate that the direction of the applied electric fields have different effect on the migration rates depending on the course of migration.

A fifth experiment was conducted to compare the efficacy of TTFields to the efficacy of Bumetanide in inhibiting glioma cells invasive potential. Bumetanide is a loop diuretic of the sulfamyl category to treat heart failure, and it is known to affect cellular motility. In the brain, bumetanide blocks the NKCC1 cation-chloride co-transporter, and thus decreases internal chloride concentration in neurons. NKCC1 provides the major pathway for Cl⁻ accumulation in glioma cells. NKCC1 localizes to the leading edge of invading processes, and pharmacologic inhibition using the loop diuretic bumetanide inhibits in vitro Transwell migration by 25% to 50%.

An invasion assay was performed as described above in connection with the second experiment with some minor modifications. More specifically, U-87 cells ($2 \times 10^5$) were suspended in serum free DMEM and seeded in the upper compartment of the chamber. The lower compartment contained 10% FBS DMEM. Both compartments contained Bumetanide in the concentration of 200 µM. TTFields were applied as described above (200 kHz, 0.6 V/cm RMS). After incubation for 24 hours at 37° C. in a 5% CO2 incubator, the cells that invaded to the bottom filter, were fixed, stained with crystal violet, and imaged under inverted microscopes. Quantification of invading cells was performed using ImageJ software (NIH).

FIG. 6 summarizes the results of the quantification for this fifth experiment. The number of invading cells was significantly reduced in cells treated by TTFields (31%) or Bumetanide (34%) applied alone (*p<0.001 from control group, student's t-test). And notably, the combined treatment using both TTFields and Bumetanide led to a synergistic 61% reduction in the number of invading cells which was significantly higher than the reduction obtained by TTFields or Bumetanide applied alone (*p<0.001, student's t-test). These results indicate that exposure to low intensities TTFields in combinations with drugs that inhibit cell motility could lead to a synergistic enhanced inhibitory effect on glioma cells invasiveness as compared to either treatment alone. And more specifically, combining TTFields with Bumetanide resulted in a synergistic enhanced efficacy as compared to either treatment alone.

The current version of Novocure's Optune® system generates AC electric fields in a target region at a single frequency, and that frequency is selected in advance to increase the effectiveness of the field at disrupting mitosis of cancer cells within the target region. As indicated above, the Optune® system sometimes reduces the strength of the electric field to prevent overheating of the patient's skin, which renders the field less effective for disrupting mitosis. The embodiments described below take advantage of two outcomes of the second and third experiment described above. More specifically, the embodiments described below take advantage of the facts that (1) the electric field intensity that is needed to cause a reduction in motility is lower than the electric field intensity that is ordinarily required for the anti-mitotic effect of TTFields; and (2) for at least certain cell lines, the frequency that provided the highest reduction in motility is different from the frequency that provides highest anti-mitotic effect.

Figure 7:
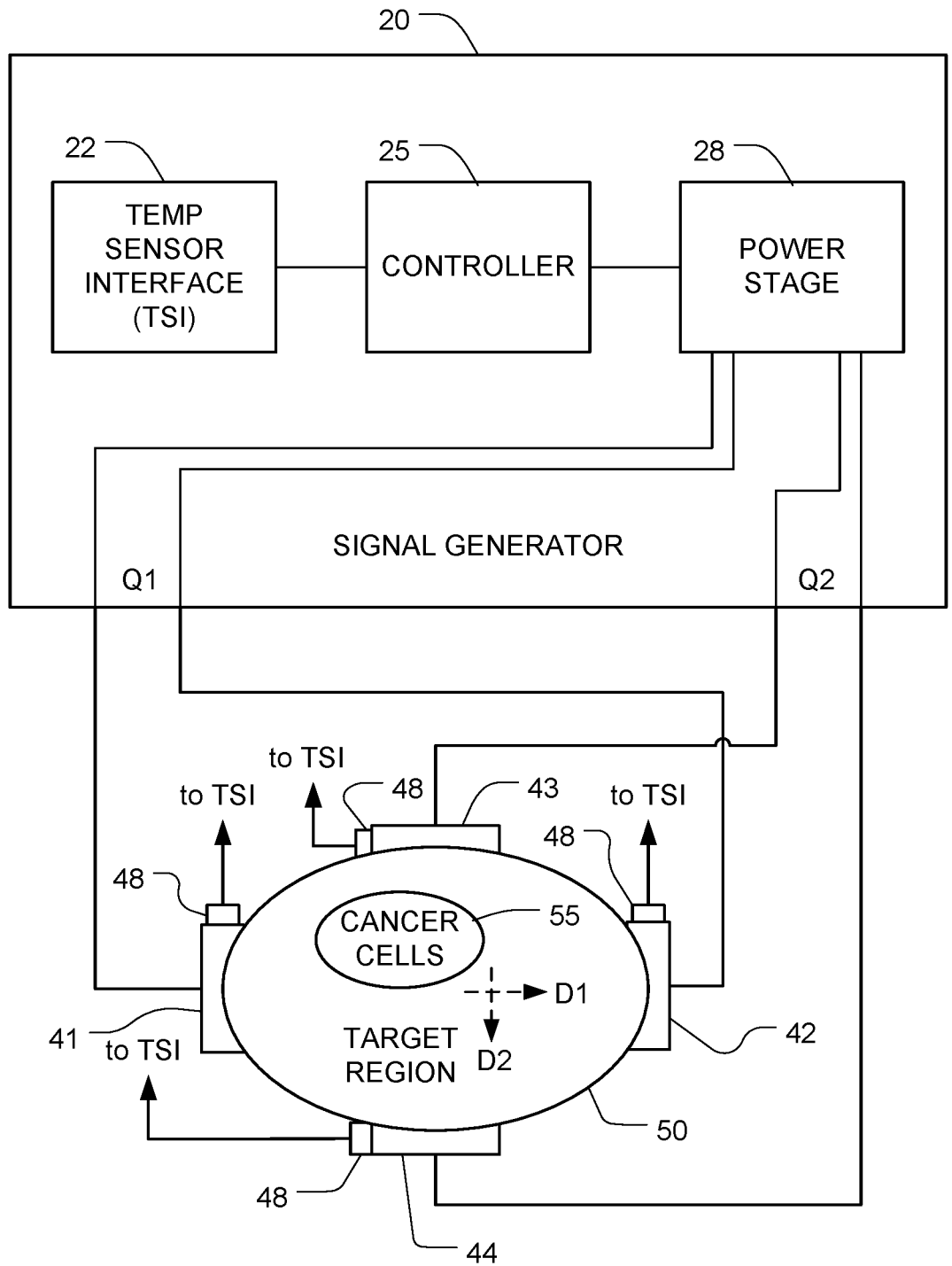
FIG. 7 depicts an embodiment of the invention that includes a signal generator and electrodes.

FIG. 7 depicts an embodiment of the invention that includes a signal generator 20 and four electrodes 41-44 (also referred to as transducer arrays). The electrodes 41-44 are positioned so that they can induce an electric field in the target region 50. For example, if the target region is a petri dish, the electrodes 41-44 may be positioned in contact with the walls of the Petri dish that contains cancer cells 55. Alternatively, if the target region is a portion of a patient's body, the electrodes 41-44 may be positioned in contact with the patient's skin in the vicinity of a tumor that includes cancer cells 55. The signal generator 20 has two outputs Q1 and Q2. The first output Q1 is connected across electrodes 41 and 42; and the second output Q2 is connected across the electrodes 43 and 44. When the signal generator 20 outputs an AC voltage at output Q1, that voltage will appear across the electrodes 41, 42 and induce an electric field in the target region 50 in a first direction D1. When the signal generator 20 outputs an AC voltage at output Q2, that voltage will appear across the electrodes 43, 44 and induce an electric field in the target region 50 in a second direction D2. Temperature sensors 48 detect the temperature at the electrodes 41-44 and report those temperatures back to a temperature sensor interface 22 contained within the signal generator 20. If the detected temperature is too high, the controller 25 will command the power stage 28 of the signal generator 20 to reduce its output voltage, which will ultimately bring the temperature down.

Note that the description of FIG. 7 in the previous paragraph is very similar to the operation of the current version of the Novocure Optune® system. But the FIG. 7 embodiment is distinguishable from Optune® because the Optune® field generator unit always outputs the same frequency. More specifically, the Optune® field generator unit always outputs a frequency that was preselected based on its anti-mitotic effect on the relevant cancer (i.e., 200 kHz in the context of glioblastoma). In contrast, the FIG. 7 embodiment switches the frequency of its outputs Q1, Q2 between a first frequency that is selected to disrupt mitosis of the cancer cells and a second frequency that is selected to reduce the motility of the cancer cells. This is accomplished in the FIG. 7 embodiment by the controller 25, which outputs appropriate control signals to the power stage 28 in order to control the frequency and amplitude of the outputs Q1 and Q2 as described below in connection with FIGS. 8-9. The controller 25 may be implemented using any of a variety of techniques that will be apparent to persons skilled in the relevant arts. Examples include but are not limited to a microprocessor or microcontroller-based controllers that are programmed to implement the sequences described herein; and hardware timers that generate appropriate control signals to orchestrate the sequences described herein. The hardware implementation of the power stage 28 is configured to respond to the control signals that are generated by the controller 25.

Figure 8:
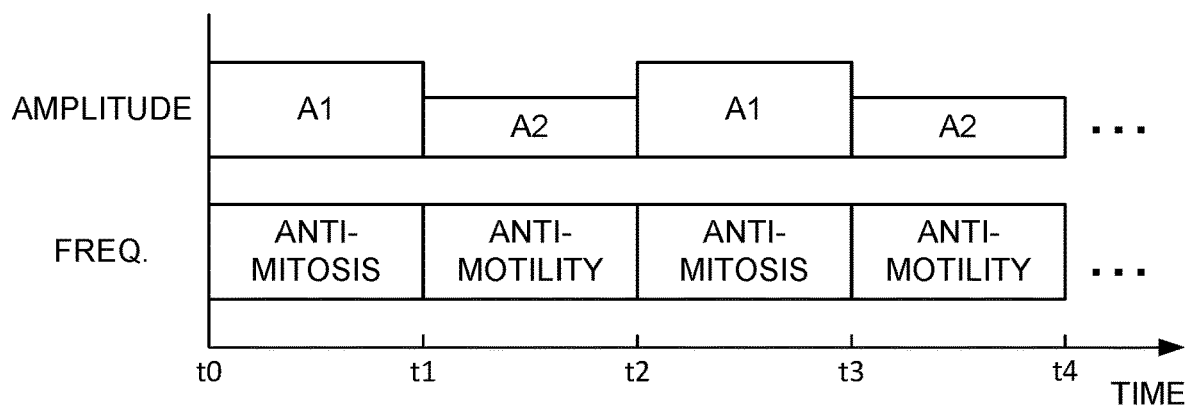
FIG. 8 depicts a first sequence of events for the outputs of the signal generator of the FIG. 7 embodiment.

FIG. 8 depicts a first sequence of events for the outputs Q1 and Q2 generated by the power stage 28 under control of the controller 25. In this sequence, the direction of the field is never switched, which means that only one of the outputs of the power stage (i.e. either Q1 or Q2) is necessary, and only one pair of electrodes (i.e., either 41/42 or 43/44) is necessary. The sequence for the lower half of FIG. 8 is as follows: First, between t0 and t1, a first AC electric field at a first frequency that is selected to disrupt mitosis of the cancer cells is imposed in the target region. Then, between t1 and t2, a second AC electric field at a second frequency that is selected to reduce motility of the cancer cells is imposed in the target region. This sequence is then repeated until the course of treatment ends.

In some embodiments, in addition to switching the frequency (as shown in the lower half of FIG. 8), the amplitude of the signal generator' output is also switched in synchrony (as shown in the upper half of FIG. 8). In these embodiments, sequence of events for the outputs generated by the power stage 28 under control of the controller 25 is as follows.

In step (a), a first AC electric field is imposed in the target region for a first interval of time (e.g., the interval between t0 and t1). The first AC electric field has a first frequency and a first amplitude, and the first frequency and the first amplitude are selected so that the first AC electric field disrupts mitosis of the cancer cells. In step (b), a second AC electric field is imposed in the target region for a second interval of time (e.g., the interval between t1 and t2). The second AC electric field has a second frequency and a second amplitude, and the second frequency and the second amplitude are selected so that the second AC electric field reduces motility of the cancer cells. The second amplitude is lower than the first amplitude. These steps (a) and (b) are then continuously repeated in an alternating sequence during a course of treatment. Optionally, additional intervening steps may be added between step (a) and step (b) or between step (b) and step (a). For example, the controller 25 may command the power stage 28 to output a third frequency between one or more instances of step (a) and step (b).

As noted above, the second amplitude (during the anti-motility phase) is lower than the first amplitude (during the anti-mitosis phase). But this is not problematic because the electric field intensity that is needed to cause a reduction in motility is lower than the electric field intensity that is ordinarily required for the anti-mitotic effect of TTFields.

And advantageously, the system can rely on the reduced amplitude during the anti-motility phase to reduce the temperature at the electrodes without reducing the field strength during the anti-mitosis phase (which requires a higher amplitude).

Furthermore, this advantage is compounded by the fact that the temperature rise is proportional to the square of the amplitude. As a result, lowering the amplitude during the anti-motility phase by X % will lower the heating during that phase to $(1-X)^2$%. For example, lowering the amplitude from 2 V/cm to 1 V/cm during the anti-motility phase will lower the heating during that phase to $(1-0.5)^2$% (i.e., to one quarter of its original value). If we assume that the anti-motility phase and the anti-mitosis phases have the same duration, this modification would reduce the overall heating load to ⅝ of its original value.

In some preferred embodiments, the second amplitude is less than 75% of the first amplitude. Preferably, both the first interval of time and the second interval of time are less than five seconds. This can be important for sustaining the anti-mitosis affect without interruption. Preferably, the course of treatment has a duration of at least 12 hours. In some preferred embodiments, the first frequency and the second frequency are different. In other embodiments, the first frequency and the second frequency could be the same (i.e., for cell lines in which the anti-mitosis frequency coincides with the anti-motility frequency). In some preferred embodiments, the first frequency (i.e., the anti-mitosis frequency) is 200 kHz±10% and the second frequency (i.e., the anti-motility frequency) is 300 kHz±10%. In some preferred embodiments, the second amplitude is at least 0.6 V/cm RMS, in order to maintain the anti-mobility effect. Optionally, a compound that inhibits cell motility (e.g., Bumetanide) may be administered during the course of treatment.

Figure 9A:
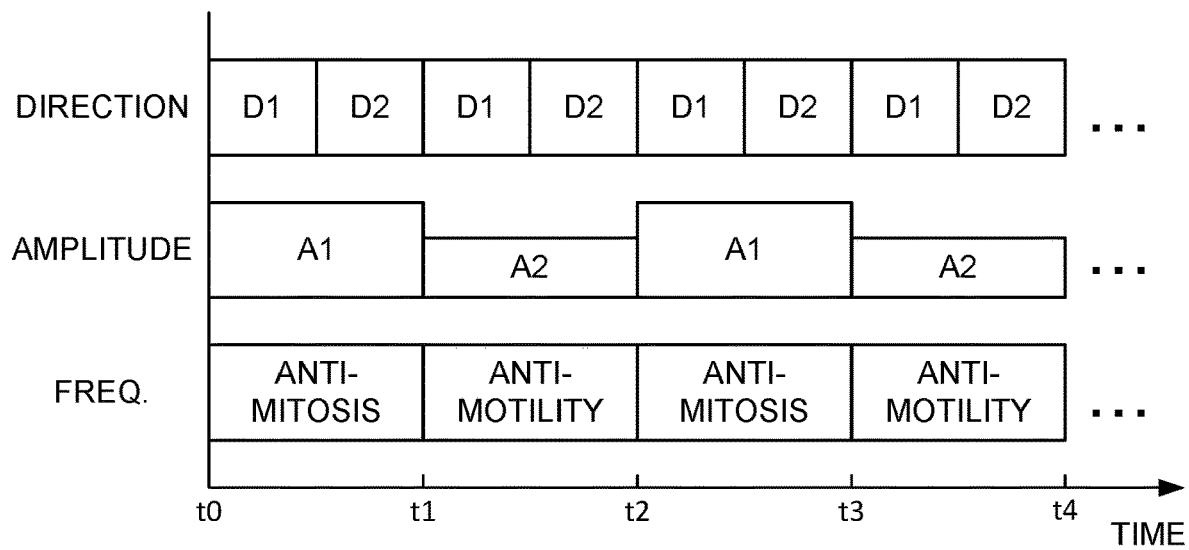
FIGS. 9A and 9B depict additional sequences of events for the outputs of the signal generator of the FIG. 7 embodiment.
Figure 9B:
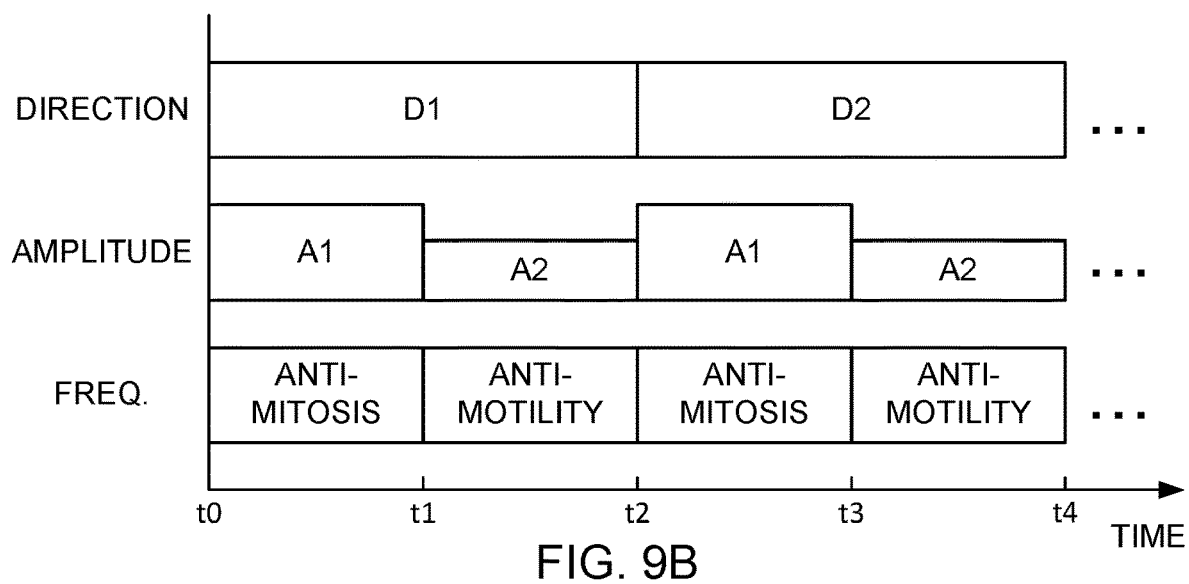

In some embodiments, in addition to switching the frequency of the field between a first frequency optimized for disrupting mitosis and a second frequency optimized for reducing motility, the direction of the electric field in the target region can also be switched between two or more directions. FIGS. 9A and 9B depict two examples in which the direction of the field is switched between the two directions D1 and D2 shown in FIG. 7. The field is generated in the direction D1 when the signal generator 20 generates its output Q1, which is applied between electrodes 41 and 42. The field is generated in the direction D2 when the signal generator 20 generates its output Q2, which is applied between electrodes 43 and 44.

FIG. 9A depicts the sequence of events for the outputs Q1 and Q2 generated by the power stage 28 of the signal generator 20 under control of the controller 25 in one such embodiment. In this sequence, the direction is switched between the two directions D1 and D2 at a rate that is faster than the rate at which the frequency is switched. The sequence here is similar to the sequence described above in connection with FIG. 8 in which both the frequency and the amplitude are switched in synchrony with each other. But in addition to switching the frequency and the amplitude as described above in connection with FIG. 8, the direction of the field is also switched. More specifically, the first AC electric field is imposed in the target region in a first direction for a first portion of the first interval of time (i.e., the first portion of the time between t0 and t1), and the first AC electric field is imposed in the target region in a second direction for a second portion of the first interval of time (i.e., the last portion of the time between t0 and t1). Preferably, the angle between the first direction D1 and the second direction D2 is between 60° and 90°. (Note that all numeric angular ranges used herein are inclusive of the endpoints.)

In some embodiments, in addition to switching the directions during the first interval of time (which corresponds to the anti-mitosis phase), the direction is also be switched during the second interval of time (which corresponds to the anti-motility phase). In these embodiments, the second AC electric field is imposed in the target region in the first direction for a first portion of the second interval of time (i.e., the first portion of the time between t1 and t2), and the second AC electric field is imposed in the target region in the second direction for a second portion of the second interval of time (i.e., the last portion of the time between t1 and t2).

FIG. 9B depicts the sequence of events for the outputs Q1 and Q2 generated by the power stage 28 under control of the controller 25 in another embodiment. In this sequence, the direction is switched between the two directions D1 and D2 at a rate that is slower than the rate at which the frequency is switched. The sequence here is similar to the sequence described above in connection with FIG. 8 in which both the frequency and the amplitude are switched in synchrony with each other. But in addition to the switching of the frequency and the amplitude described above in connection with FIG. 8, the direction of the first AC electric field is changed during at least some of the repeating steps, and the direction of the second AC electric field is also changed during at least some of the repeating steps. In the example of FIG. 9B, the original sequence corresponds to the interval of time between t0 and t2, and that original sequence is repeated during the course of the treatment, with the first repetition occupying the interval of time between t2 and t4. As seen in FIG. 9B, the direction of the fields for both the anti-mitosis stage and the anti-migration stage was switched to D2 during the first repetition with respect to the original sequence.

Note that in the sequences depicted in FIGS. 8-9 above, the anti-mitosis phase and the anti-motility phase are mutually exclusive with respect to time. However, in alternative embodiments, those phases may overlap with each other either partially or completely. An example of such an embodiment would be to implement the following two steps (a) and (b) simultaneously: In step (a), a first AC electric field is imposed in the target region. The first AC electric field has a first frequency and a first amplitude that are selected so that the first AC electric field disrupts mitosis of the cancer cells. In step (b), a second AC electric field is imposed in the target region. The second AC electric field has a second frequency and a second amplitude that are selected so that the second AC electric field reduces motility of the cancer cells. The second frequency and the first frequency are different, and the second amplitude is lower than the first amplitude. When steps all (a) and (b) are implemented simultaneously, the first and second AC electric fields will add by superposition.

Some embodiments are directed to a method for treating cancer by exposing the primary tumor or its vicinity, metastases, or organs with high probability of metastatic uptake to alternating electric fields at a frequency optimally picked to inhibit the migration or invasion of the tumor cells. At least for certain cell lines, this frequency is significantly different from the frequency required to disrupt mitosis. The field may be delivered using Novocure's Optune® system or the devices described in U.S. Pat. Nos. 7,089,054, 6,868,289, and 7,706,890, which are incorporated herein by reference. It may be used to treat GBM or other types of cancer. The field may be delivered in a preferential direction, and the preferential direction chosen to prevent progression into non-resectable areas, or vital organs.

For different types of cancer, the optimal frequency for inhibiting cell migration of a specific cancer cell type may be determined by culturing the cells (or a cell line that closely resembles the cells of interest) in petri dishes, exposing the cells to alternating electric fields at a given intensity, and at different frequencies, and finding the frequency that has the maximal inhibitory effect on cell migration for this specific cell line. The effect of the electric field may be determined via scratch assays and/or via an invasion assay.

Some embodiments are directed to a method for treating cancer, whereby the tumor is exposed to alternating electric fields containing components at two frequencies: One frequency is the frequency that is optimal to inhibit cell division, and the other frequency optimal to inhibit migration. Note that combining two different frequencies tuned to damage dividing cells is described in U.S. Pat. No. 8,244,345, which is incorporated herein by reference. But here, one of the frequencies is tuned to prevent migration instead. The signals at the different frequencies may be applied sequentially, or they may be combined into a single field. The fields may be delivered in one direction or a plurality of different directions.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of inhibiting spreading of cancer cells in a target region, the method comprising:
   (a) imposing a first AC electric field in the target region for a first interval of time, the first AC electric field having a first frequency and a first amplitude, wherein the first frequency and the first amplitude are selected so that the first AC electric field disrupts mitosis of the cancer cells;
   (b) imposing a second AC electric field in the target region for a second interval of time, the second AC electric field having a second frequency and a second amplitude, wherein the second frequency and the second amplitude are selected so that the second AC electric field reduces motility of the cancer cells, and wherein the second amplitude is lower than the first amplitude; and
   (c) continuously repeating step (a) and step (b) in an alternating sequence during a course of treatment.

2. The method of claim 1, wherein the second amplitude is less than 75% of the first amplitude.

3. The method of claim 2, wherein the first interval of time is less than 5 seconds, and wherein the second interval of time is less than 5 seconds.

4. The method of claim 3, wherein the course of treatment has a duration of at least 12 hours.

5. The method of claim 1, wherein the second frequency and the first frequency are different.

6. The method of claim 1, wherein the first frequency is 200 kHz±10% and the second frequency is 300 kHz±10%.

7. The method of claim 1, further comprising a step of administering a compound that inhibits cell mobility during the course of treatment.

8. The method of claim 7, wherein the compound comprises Bumetanide.

9. The method of claim 1, wherein the second amplitude is at least 0.6 V/cm RMS.

10. The method of claim 1, wherein the second amplitude is less than 75% of the first amplitude, wherein the second frequency and the first frequency are different, wherein the first interval of time is less than 5 seconds, wherein the second interval of time is less than 5 seconds, and wherein the second amplitude is at least 0.6 V/cm RMS.

11. The method of claim 10, wherein the first frequency is 200 kHz±10% and the second frequency is 300 kHz±10%.

12. The method of claim 1, wherein the first AC electric field is imposed in the target region in a first direction for a first portion of the first interval of time,
   wherein the first AC electric field is imposed in the target region in a second direction for a second portion of the first interval of time, and
   wherein an angle between the first direction and the second direction is between 60° and 90°.

13. The method of claim 12, wherein the second AC electric field is imposed in the target region in the first direction for a first portion of the second interval of time, and
   wherein the second AC electric field is imposed in the target region in the second direction for a second portion of the second interval of time.

14. The method of claim 13, wherein the second amplitude is less than 75% of the first amplitude.

15. The method of claim 14, wherein the second frequency and the first frequency are different, wherein the first interval of time is less than 5 seconds, and wherein the second interval of time is less than 5 seconds.

16. The method of claim 1, wherein a direction of the first AC electric field is changed during at least some of the repeating steps, and wherein a direction of the second AC electric field is changed during at least some of the repeating steps.

17. The method of claim 16, wherein the second amplitude is less than 75% of the first amplitude.

18. The method of claim 17, wherein the second frequency and the first frequency are different, wherein the first interval of time is less than 5 seconds, and wherein the second interval of time is less than 5 seconds.

19. An apparatus for inhibiting spreading of cancer cells in a target region, the apparatus comprising:
   an AC signal generator having (i) a first controllable output configured to apply an AC voltage across a first set of capacitively coupled electrodes that are positioned in a vicinity of the target region, so as to impose an electric field in the target region in a first direction and (ii) a second controllable output configured to apply an AC voltage across a second set of capacitively coupled electrodes that are positioned in the vicinity of the target region, so as to impose an electric field in the target region in a second direction; and
   a controller configured to (a) control the first controllable output so that a first AC signal is generated for a first interval of time, the first AC signal having a first frequency and a first amplitude, wherein the first frequency and the first amplitude are selected to impose an electric field that disrupts mitosis of the cancer cells, and (b) control the first controllable output so that a second AC signal is generated for a second interval of time, the second AC signal having a second frequency and a second amplitude, wherein the second frequency and the second amplitude are selected to impose an electric field that reduces motility of the cancer cells, and wherein the second amplitude is lower than the first amplitude, (c) control the second controllable output so that a third AC signal is generated for a third interval of time, the third AC signal having a third frequency and a third amplitude, wherein the third frequency and the third amplitude are selected to impose an electric field that disrupts mitosis of the cancer cells, and (d) control the second controllable output so that a fourth AC signal is generated for a fourth interval of time, the fourth AC signal having a fourth frequency and a fourth amplitude, wherein the fourth frequency and the fourth amplitude are selected to impose an electric field that reduces motility of the cancer cells, and wherein the fourth amplitude is lower than the third amplitude, and (e) continuously repeat (a) through (d) in an alternating sequence during a course of treatment.

20. The apparatus of claim 19, wherein the second amplitude is less than 75% of the first amplitude and wherein the fourth amplitude is less than 75% of the third amplitude.

21. The apparatus of claim 19, wherein the second frequency and the first frequency are different, and wherein the fourth frequency and the third frequency are different.

22. The apparatus of claim 19, wherein the second amplitude is less than 75% of the first amplitude and wherein the fourth amplitude is less than 75% of the third amplitude, wherein the second frequency and the first frequency are different, wherein the fourth frequency and the third frequency are different, wherein the third frequency is the same as the first frequency, wherein the fourth frequency is the same as the second frequency, wherein the first interval of time is less than 5 seconds, wherein the second interval of time is less than 5 seconds, wherein the third interval of time is less than 5 seconds, and wherein the fourth interval of time is less than 5 seconds.

23. The apparatus of claim 19, wherein the first frequency is 200 kHz±10%, the second frequency is 300 kHz±10%, the third frequency is 200 kHz±10%, and the fourth frequency is 300 kHz±10%.

* * * * *